US010137238B2

(12) United States Patent
Spool et al.

(10) Patent No.: US 10,137,238 B2
(45) Date of Patent: Nov. 27, 2018

(54) METHOD OF STORING BOTH NEW AND USED PEN NEEDLES

(71) Applicant: Becton, Dickinson and Company, Franklin Lakes, NJ (US)

(72) Inventors: Ira Spool, Newton, MA (US); Cole Constantineau, Cambridge, MA (US); Ryan Schoonmaker, Oceanside, CA (US); Sean P. Sullivan, Ridgewood, NJ (US); Abhijitsinh Raj, Morris Plains, NJ (US); Michel Bruehwiler, Newton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 439 days.

(21) Appl. No.: 14/949,831

(22) Filed: Nov. 23, 2015

(65) Prior Publication Data

US 2016/0074572 A1    Mar. 17, 2016

Related U.S. Application Data

(62) Division of application No. 13/204,632, filed on Aug. 5, 2011, now Pat. No. 9,216,253.

(Continued)

(51) Int. Cl.
*A61M 5/00* (2006.01)
*A61M 5/24* (2006.01)
*A61M 5/32* (2006.01)

(52) U.S. Cl.
CPC .......... *A61M 5/002* (2013.01); *A61M 5/3202* (2013.01); *A61M 5/3205* (2013.01);

(Continued)

(58) Field of Classification Search
CPC ........ B65D 85/02; B65D 83/24; A61M 5/002; A61M 5/003; A61M 5/008; A61M 5/3202; A61M 5/3205

(Continued)

(56) References Cited

U.S. PATENT DOCUMENTS 2,467,678 A    4/1949 Lockhart
2,601,065 A    6/1952 Son (Continued)

FOREIGN PATENT DOCUMENTS

EP    0504538 A1    9/1992
EP    0697222 A2    2/1996

(Continued)

*Primary Examiner* — Stephen F Gerrity
(74) *Attorney, Agent, or Firm* — Dickinson Wright PLLC

(57) ABSTRACT

A flip-open multi-pack assembly which contains a plurality of new pen needles via a rectangular or tube-shaped, hinged shell housing, wherein new pen needles are stored in a plurality of user accessible openings each having a sterility barrier formed by covers that cover the non-patient end of the openings where the new pen needles are contained. Used pen needles are returned and stored in openings accessible by rotatably opening the shell housing. One or more of the openings within first and second opposite ends of the housing shell include a slidable internal holder configured to releasably secure the inner shield of the new pen needle, and subsequently be pulled forward when the new pen needle is removed and locked at a forward position, to create an interior space, accessible from an opposite end when the hinged housing is opened, for a used pen needle to be inserted and stored.

9 Claims, 17 Drawing Sheets

Related U.S. Application Data

(60) Provisional application No. 61/344,539, filed on Aug. 16, 2010, provisional application No. 61/344,536, filed on Aug. 16, 2010.

(52) U.S. Cl.
CPC ............. *A61M 5/003* (2013.01); *A61M 5/008* (2013.01); *A61M 5/24* (2013.01)

(58) Field of Classification Search
USPC ............................................. 53/246; 206/366
See application file for complete search history.

(56) References Cited

U.S. PATENT DOCUMENTS

| | | | |
|---|---|---|---|
| 2,726,759 A | 12/1955 | Fleming | |
| 3,074,540 A | 1/1963 | Beich et al. | |
| 3,114,455 A | 12/1963 | Claisse et al. | |
| 3,155,264 A | 11/1964 | Shook | |
| 3,439,796 A | 4/1969 | Zykoski | |
| 4,126,239 A | 11/1978 | Gehrig et al. | |
| 4,139,093 A | 2/1979 | Holmes | |
| 4,919,264 A | 4/1990 | Shinall | |
| 5,090,564 A | 2/1992 | Chimienti | |
| 5,325,965 A | 7/1994 | Kelley | |
| 5,330,899 A | 7/1994 | Devaughn | |
| 5,626,230 A | 5/1997 | Shanley et al. | |
| 5,829,589 A | 11/1998 | Nguyen et al. | |
| 5,873,462 A | 2/1999 | Nguyen et al. | |
| 6,346,094 B2 * | 2/2002 | West et al. | A61M 5/002 206/365 |
| 6,783,003 B2 | 8/2004 | Simm et al. | |
| 7,654,981 B2 * | 2/2010 | Lehmann | A61M 5/3205 206/366 |
| 7,694,822 B2 | 4/2010 | Sullivan et al. | |
| 8,550,240 B2 | 10/2013 | Marcus et al. | |
| 9,016,472 B2 | 4/2015 | Van Der Beek et al. | |
| 2002/0014430 A1 | 2/2002 | Groth | |
| 2003/0015444 A1 | 1/2003 | Molin et al. | |
| 2006/0032769 A1 | 2/2006 | Erickson et al. | |
| 2007/0151973 A1 | 7/2007 | Wang | |
| 2008/0108951 A1 | 5/2008 | Jerde et al. | |
| 2011/0060292 A1 * | 3/2011 | Schraga | A61M 5/3205 206/366 |

FOREIGN PATENT DOCUMENTS

| | | | | |
|---|---|---|---|---|
| FR | 2671730 A1 | 7/1992 | | |
| GB | 1409081 A | * 10/1975 | | B65D 85/24 |
| JP | 41726 | 12/1916 | | |
| JP | 35004998 A | 3/1960 | | |
| JP | H06321268 A | 11/1994 | | |
| JP | 08066475 A | * 3/1996 | | A61M 5/3205 |
| JP | 2000262616 A | 9/2000 | | |
| JP | 2000271219 A | 10/2000 | | |
| JP | 2003533291 A | 11/2003 | | |
| JP | 2003533292 A | 11/2003 | | |
| JP | 2008066475 A | 3/2008 | | |
| JP | 2013-521028 | 6/2013 | | |
| WO | WO-0054691 A1 | 9/2000 | | |
| WO | WO-0187387 A1 | 11/2001 | | |
| WO | WO-0211797 A1 | 2/2002 | | |
| WO | WO-03080467 A1 | 10/2003 | | |
| WO | WO 2009016161 A1 * | 2/2009 | | A61M 5/008 |

* cited by examiner

METHOD OF STORING BOTH NEW AND USED PEN NEEDLES

CROSS-REFERENCE TO RELATED APPLICATIONS

This application is a division of U.S. patent application Ser. No. 13/204,632, filed on Aug. 5, 2011, which claims the benefit of U.S. Provisional Patent Application Ser. Nos. 61/344,536 and 61/344,539, both filed on Aug. 16, 2010, the disclosures of each of said prior applications being incorporated herein by reference in its entirety.

FIELD OF THE INVENTION

The present invention relates to a storage assembly for pen needles of an injection apparatus. More particularly, the present invention relates to a storage assembly for storing both new and used pen needles of an injection apparatus.

BACKGROUND OF THE INVENTION

In certain circumstances, it is desirable to inject medication directly into human tissue. Typically, syringes or pen injection devices are used to inject medicaments into tissue areas, such as the intramuscular tissue layer, the subcutaneous tissue layer, and the intradermal tissue layer. The assembly and operation of such a pen injection device is described in U.S. Pat. No. 7,645,264, issued Jan. 12, 2010, the entire contents of which is hereby incorporated herein by reference.

Pen injection devices, such as the exemplary drug delivery pen 10 as shown in FIG. 1, provide the user a convenient way to carry a medicament supply. All of the required features and components for at least a single use are provided in the assembly, and in most cases, provide for multiple uses. To do so, the pen 10 typically comprises a dose knob/button 24, an outer sleeve 13, and a cap 21. The cap 21 covers a proximal end of the pen 10 and an injection needle attached thereto, and is used by the user to securely hold the drug delivery pen 10 in a shirt pocket, purse or other suitable location. The dose knob/button 24 allows a user to set the dosage of medication to be injected, and the outer sleeve 13 contains the driving mechanisms and supply, and further provides a gripping surface for the user to grip when injecting medication.

FIG. 2A is an exploded view of the exemplary drug delivery pen 10 shown in FIG. 1, and typical components contained therein. At a distal end, the dose knob/button 24 is provided and has a dual purpose. The dose knob/button 24 is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail herein as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used.

FIGS. 2B and 2C are perspective views of the pen needle of FIG. 2A in greater detail. As shown in FIG. 2B, the pen needle includes the hub 20 disposed at a non-patient end thereof which includes a plurality of ribs 64 for engagement with anti-rotation/retaining structures that will be described in greater detail below. In addition, protrusion 68 extends from a patient end of the hub 20 and the patient needle 11 extends from the protrusion 68. The septum-penetrating needle cannula 18 disposed within the non-patient end of the hub 20 fluidly communicates with the patient needle 11. Further, as shown in FIG. 2C, the interior of the non-patient end of the hub 20 includes threads 72 for connection with the pen injector. FIGS. 2A-2C illustrate one example of a pen needle.

To protect a user, or anyone who handles the drug delivery pen 10, an outer cover 69, which attaches to the hub 20, covers the hub when not in use. An inner shield 59 covers the patient needle 11 within the outer cover 69. The inner shield 59 can be secured to the hub 20 to cover the patient needle 11 by any suitable means, such as an interference fit or a snap fit. The cap 21 fits snugly against outer sleeve 13 to allow a user to securely carry the drug delivery pen 10. At a time of use, the cap 21, outer cover 69 and inner shield 59 are removed to expose the hub 20.

The medicament cartridge 12 is typically a tube sealed at one end with the septum 16 and sealed at the other end with the stopper 15. The septum 16 is pierceable by the septum penetrating cannula 18 in the hub 20, but does not move with respect to the medicament cartridge 12. The stopper 15 is axially displaceable within the medicament cartridge 12 to deliver the desired medicament amount while maintaining a fluid tight seal.

A pen needle, which includes the hub 20, needle 11, outer cover 69 and inner shield 59, is typically used for a single injection and is then disposed of. Typically, new pen needles are packaged individually and disposed loose in a container, such as a box or carton. Each pen needle is sealed in a package formed by the outer cover with a label covering the opening in the outer cover to identify the pen needle and provide a sterility barrier. However, containers of such packaged new pen needles do not include means for easily dispensing the new pen needles or containing used pen needles. Accordingly, a need exists for a storage assembly that easily dispenses new pen needles and stores both new and used pen needles.

Additionally, existing pen needle containers are configured to store a large number of packaged new pen needles. The large number of packaged new pen needles causes these containers to be large and bulky, such that the containers are not conducive to being carried by the user. Accordingly, a need exists for a storage assembly that is conveniently carried by a user.

SUMMARY OF THE INVENTION

In accordance with aspects of exemplary embodiments of the present invention, the above and other problems are substantially solved by providing a multi-pack assembly for containing and dispensing one or more new pen needles, and receiving and then safely and securely storing used pen needles after use.

In accordance with an aspect of the present invention, a housing shell is provided in which a plurality of both new and used pen needles can be contained. An exemplary embodiment of such a shell can be, but is not limited to, a square shape, a rectangular shape, a round shape, a cylindrical shape, or an elliptical shape.

In accordance with another aspect of the present invention, the housing shell can be provided with first and second opposite containment ends which are attached via a hinge or other flexible member to allow one containment end to rotate relative to the opposite containment end such that an interior of the housing shell can be accessed by opening, and secured by closing, of the hinge.

In accordance with another aspect of the present invention, one or both of the first and second opposite containment ends can comprise one or more openings, which are configured to contain and store new and used pen needles which can be accessed by a user with or without opening the hinge.

In accordance with another aspect of the present invention, each of the openings of the first and second opposite containment ends should comprise a sterility barrier, such as those formed by providing covers that cover the openings and the non-patient ends of the new pen needles contained within the housing shell, and which are connected to the housing shell.

In accordance with another aspect of the present invention, each of the openings of the first and second opposite containment ends can comprise a tortuous path or inner shield on the patient end of each pen needle, wherein, in an exemplary embodiment of the present invention, the shield on the patient end of each pen needle is also used to releasably secure the new pen needle in each opening. Removal of the needle is achieved either through the release of the needle and shield together from the housing shell, requiring the user to remove the shield before use, or through the release of the needle from the shield leaving the shield in the housing shell.

In accordance with another aspect of the present invention, each of the openings of the first and second opposite containment ends can pass through the entire length of each end, respectively, such that one end of the opening can access a new pen needle and an opposite end of the opening can be used to store a used pen needle.

In accordance with another aspect of the present invention, each of the openings of the first and second opposite containment ends can pass through the entire length of each ends, respectively, such that the housing shell can be provided with the hinge that when opened, rotates the first and second opposite containment ends of the housing shell and allows interior access to openings of the first and second opposite containment ends for receiving and storing used pen needles.

In accordance with another aspect of the present invention, one or more of the openings within each of the first and second opposite containment ends of the housing shell can be provided with one or more protrusions for holding the pen needle in some manner thereby preventing rotation of the new pen needle during removal, and preventing rotation of the used pen needle during insertion, to allow the pen needle to be attached and detached from the pen and from the housing shell.

In accordance with another aspect of the present invention, the one or more openings within each of the first and second opposite containment ends of the housing shell can be provided with a slidable internal holder which is configured to releasably secure the inner shield of the new pen needle, and to then be pulled forward some distance through the opening when the new pen needle is removed and lock at a forward position, and thereby create a space in the opening, opposite the new pen needle removal side and accessible from the opposite, hinged side, for a used pen needle to be inserted and stored.

In accordance with another aspect of the present invention, a multi-pack assembly for containing and then dispensing one or more new pen needles, and receiving and then safely and securely storing used pen needles, can be provided wherein during an exemplary use a user first grips an outer surface of the housing shell and removes a cover to access a new pen needle secured within the covered opening of one of the first or second containment ends of the assembly. The user can then attach the accessible new pen needle to the drug delivery pen, such as through the use of a threading action, as the new pen needle is releasably secured within the opening and prevented from rotating. The user can then pull the new pen needle from the assembly to remove the new pen needle, and such removal motion serves to pull the slidable internal holder component within the multi-pack assembly forward, thereby creating a space at an opposite end for the subsequent used pen needle to be inserted and stored. The user can then simply remove the shield that is shielding the new pen needle and perform the injection. If the shield is left in the housing shell during removal, the user can simply perform the injection.

In accordance with another aspect of the present invention, a multi-pack assembly for containing and then dispensing one or more new pen needles, and receiving and then safely and securely storing used pen needles, can be provided wherein upon completion of the injection, the user can open the multi-pack assembly at the hinged point between the opposite first and second containment ends to allow interior access to the created opening for receiving and storing the used pen needle, and place the used pen needle into the open space, engaging the anti-rotation feature, and unscrewing the pen injection device from the used pen needle and leaving the used pen needle in the opening of the multi-pack assembly. After the used pen needle has been unscrewed from the device, the user can then simply close the shell of the multi-pack assembly for storage.

In accordance with another aspect of the present invention, a multi-pack assembly for containing and then dispensing one or more new pen needles, and receiving and then safely and securely storing used pen needles, can be provided by a device including a plurality of pen needles individually contained in a tube-shaped structure. A sterility barrier for each new pen needle should be provided and is formed by covers that cover a non-patient end of each pen needle. Each pen needle is contained in a separate, individually accessible section or unit of the tube structure, and adjacent units of the tube structure are hingedly connected.

These and other objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will become more apparent from the following detailed description of exemplary embodiments of the present invention and from the accompanying figures, in which.

Throughout the drawings, like reference numbers will be understood to refer to like parts, components and structures.

DETAILED DESCRIPTION OF THE EXEMPLARY EMBODIMENTS

Figure 1:
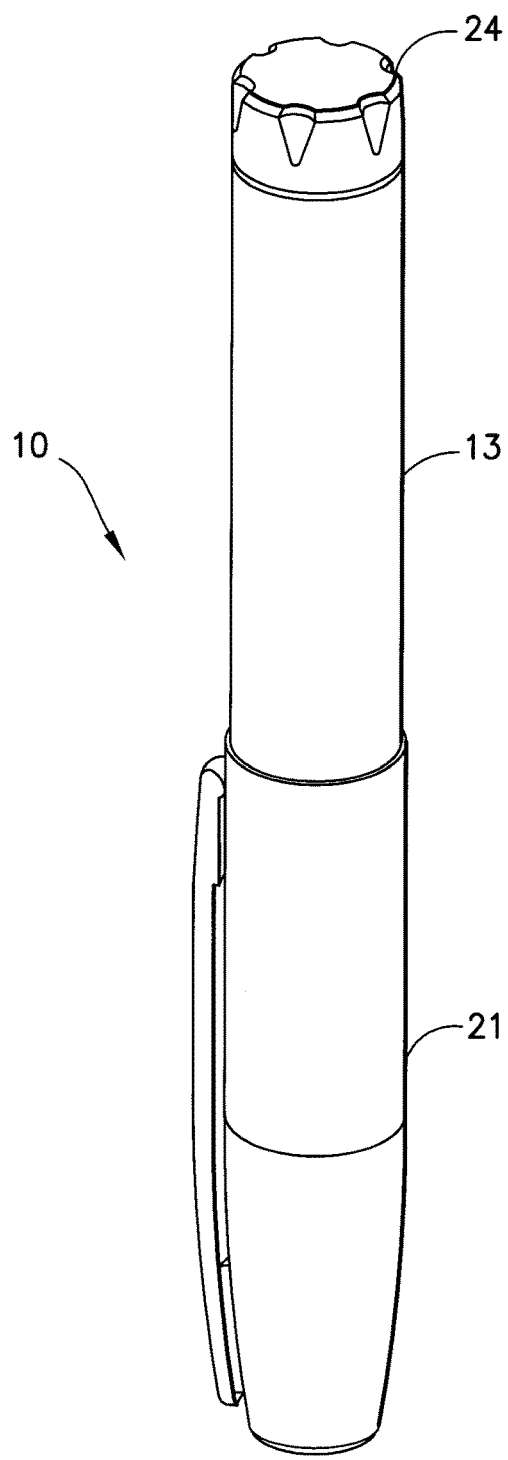
FIG. 1 is a perspective view of an assembled drug delivery pen for use with exemplary embodiments of the present invention.

As noted above, new pen needles are typically packaged individually and disposed loose in a container, such as a box or carton. Each pen needle is sealed in a package formed by the outer cover with a label covering the opening in the outer cover to identify the pen needle and provide a sterility barrier. However, containers of such packaged new pen needles do not include means for easily dispensing the new pen needles or containing used pen needles. Additionally, existing pen needle containers are configured to store a large number of packaged new pen needles. The large number of packaged new pen needles causes these containers to be large and bulky, such that the containers are not conducive to being carried by the user.

Current pen needles are sold individually packaged inside a plastic cover, with a label adhered to the cover to identify the needle and provide a sterility barrier. However, a more convenient system and method is desired including a multiple needle package configuration that stores and provides new pen needles for use, and includes some provision for receiving and containing used pen needles after use. The exemplary embodiments of the present invention address these and other needs by providing a multi-pack assembly including multiple new pen needles in user accessible openings of the assembly, wherein covers or other enclosures are provided or positioned to enclose each new pen needle inside the user accessible openings of the assembly. In one or more exemplary embodiments, hinged access to an opposite end of the accessible openings is provided to receive and store used pen needles after removal of the new pen needles. In one or more other exemplary embodiments, hinged access to an opposite end of the accessible openings is provided to access a next new pen needle.

In an exemplary embodiment of the present invention shown in FIGS. 3-8, a multi-pack assembly is provided for storing and then dispensing one or more new pen needles from spaces accessible from one end, and receiving and containing used pen needles in substantially the same spaces accessible from an opposite end once the space is opened by the removal of the new pen needle. The embodiments include a flip-open multi-pack assembly which can contain a plurality of new pen needles, such as through the provision of a rectangular shaped, hinged shell housing, wherein new pen needles can be stored in a plurality of covered, user accessible openings, each having a sterility barrier formed, for example, by covers that cover the user accessible openings and non-patient ends of the new pen needles contained therein which are releasably secured to an inner portion of each opening of the shell via a tortuous path shield on the patient end of each new pen needle. Removal of the needle is achieved either through the release of the needle and shield together from the housing shell, requiring the user to remove the shield before use, or through the release of the needle from the shield, leaving the shield in the housing shell. When left on the needle, the shield provides sterility to the patient end, via the tortuous path, but when left in the housing shell, it does not require the user to remove it after attachment of the needle.

The exemplary hinged shell housing of embodiments of the present invention include a substantially enclosed housing having up to a first and second containment end connected via a hinge or other flexible member, and which are configured to rotate relative to each other. Such a hinge, when opened, allows interior access to the openings within one or both of the first and second containment ends of the housing for receiving and storing used pen needles. One or more of the openings within each of the first and second opposite containment ends of the housing can be provided with one or more protrusions for preventing rotation of the new pen needle contained therein, or the used pen needle inserted therein, to allow the pen needle to be attached and detached from the pen and from the housing shell. Further, one or more of the openings within each of the first and second opposite containment ends of the housing shell can be provided with a slidable internal holder which is configured to releasably secure the shield of the new pen needle, and to then be pulled forward when the new pen needle is removed and lock at a forward position, and thereby create a space, accessible from the opposite, hinged end, for a used pen needle to be inserted and stored.

Pen needles of the exemplary embodiments can be manufactured using existing processes and subsequently assembled into the housings of the exemplary embodiments of the present invention, thereby simplifying the manufacturing process. The overall size of the exemplary embodiments of the present invention is minimized by allowing used pen needles to be stored in substantially the same spaces previously used to store the new needles. Further, the exemplary embodiments of the present invention can be constructed having a size and shape, and contoured edges, to increase the comfort of the user during transportation, such as in a user's pocket.

Figure 3:
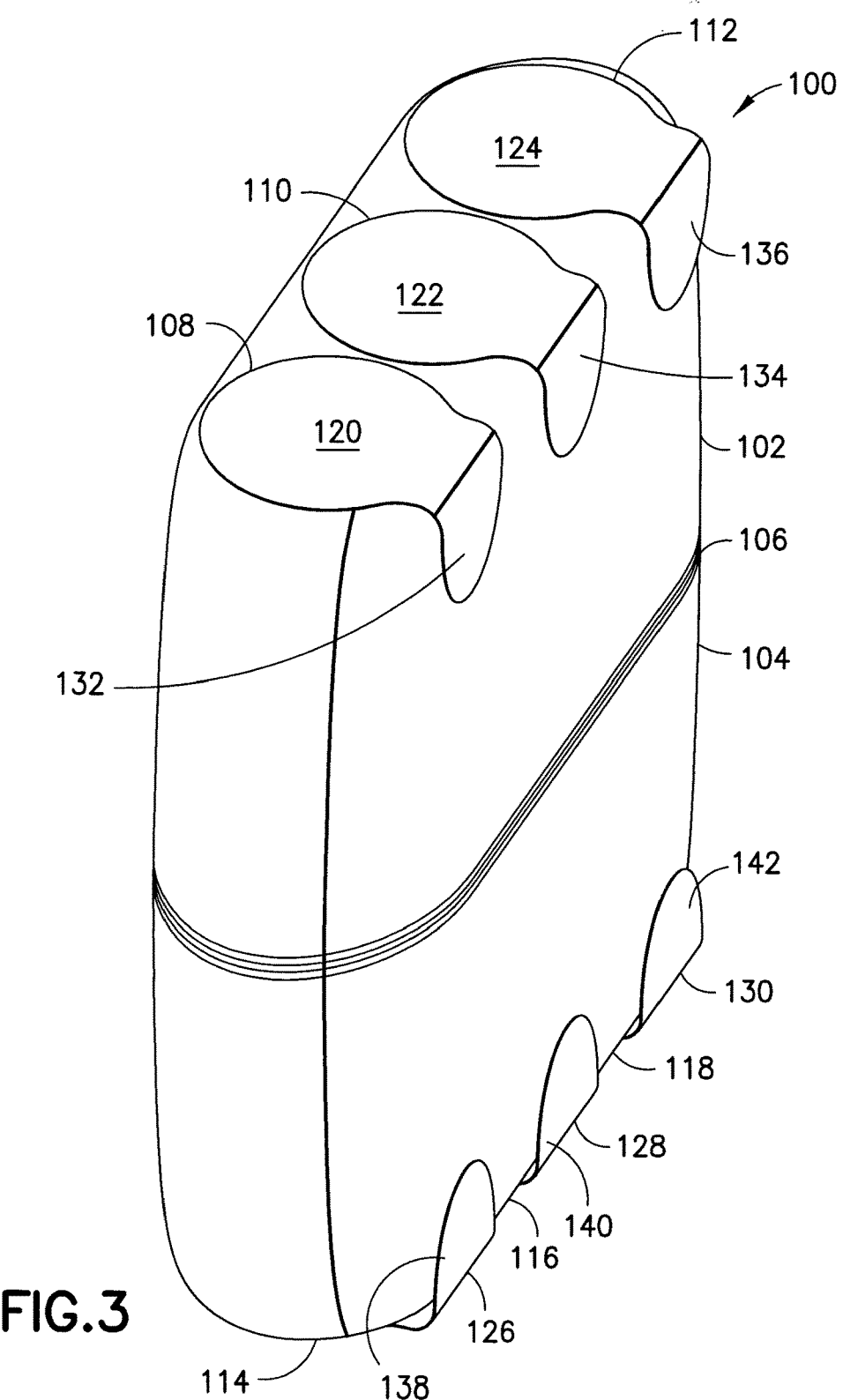
FIG. 3 is a perspective view of a flip-open multi-pack assembly according to an exemplary embodiment of the present invention.

An exemplary hinged shell housing 100 is shown in FIG. 3. In a first exemplary embodiment of the present invention, the housing 100 comprises a first and second containment end, 102 and 104, respectively, that are rotatably joined at a point 106. In the exemplary embodiment shown, the first and second containment ends 102 and 104 are rotatably joined at the point 106 using a flexible member, such as a hinge including but not limited to, a barrel hinge, living hinge or other suitable hinge mechanism. In yet other embodiments of the present invention, the first and second containment ends 102 and 104 can be snap fit together at the point 106 using a detent and recess arrangement (not shown). Still other embodiments of the present invention can use any number of other connection means between the first and second containment ends 102 and 104 of the housing 100. Further, exemplary embodiments of the present invention can comprise a single containment end, either 102 or 104, and a simple hinged cover (not shown) in place of the omitted containment end.

One or both of the first and second containment ends 102 and 104 of the housing 100 can provide access to new pen needles contained therein via covered openings 108-118. Each of the openings 108-118 of the first and second opposite containment ends 102 and 104 pass through the entire length of each end, respectively, such that one end of the opening can be used to access a new pen needle contained in the opening, and an opposite end of the opening can be used to store a used pen needle. The shell housing 100 can be provided with a hinge that when opened, rotates the first and second opposite containment ends 102 and 104 of the housing and allows interior access to openings of the first and second opposite containment ends for receiving and storing used pen needles.

A sterility barrier to each new pen needle in openings 108-118 should be provided via covers 120-130 which are disposed to cover the openings 108-118 and the new pen needles contained therein. The sterility barriers can be constructed of paper, metal foil, plastic or similar materials, and can be attached to cover the openings via adhesive, heat seal, ultrasonic welding or other suitable means, and each of the covers 120-130 can be provided with a tab element 132-142 to allow a user to easily grasp and remove the tabs and covers 120-130. In an exemplary embodiment of the present invention, the tab elements 132-142 can be provided with a different degree of adhesion, to allow a user to easily grasp and lift the tabs and covers 120-130. The covers 120-130 can be further provided with colors, marks or other indicators of the pen needle contained therein.

Figure 4:
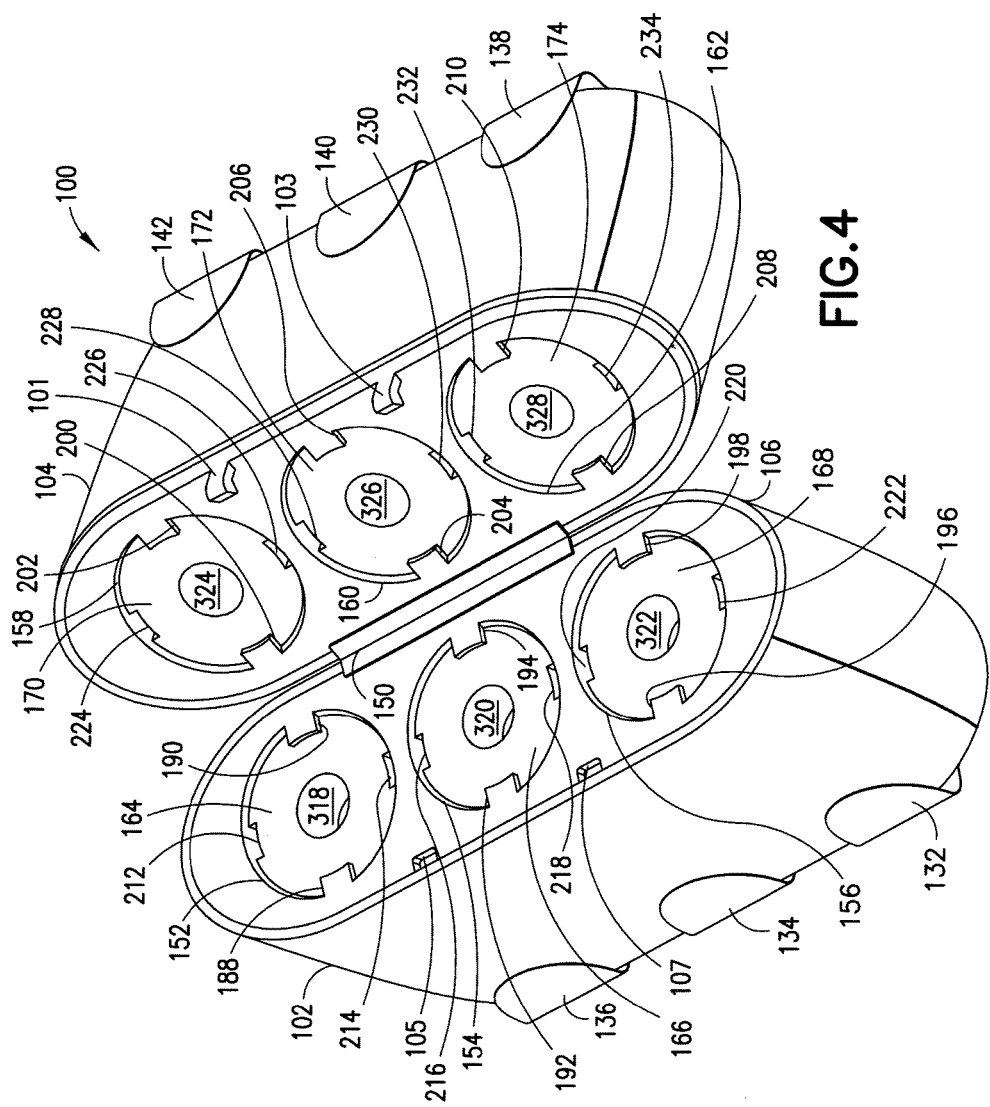
FIG. 4 is a perspective view of the multi-pack assembly of FIG. 3 opened at the hinge according to an exemplary embodiment of the present invention.

FIG. 4 illustrates the exemplary shell housing 100 that has been opened to show the facing surfaces of the first and second containment ends 102 and 104 of the shell housing 100, and the interior access to the openings. In the condition illustrated in FIG. 4, no spaces have been yet created in the openings for the placement of used pen needles. That is, the condition illustrated in FIG. 4 represents an exemplary shell housing 100 in which each opening is containing a new pen needle. It is the removal of at least one new pen needle that creates an opening space accessible from the interior for the insertion of the used pen needle.

In the exemplary embodiment shown, a hinge 150 is provided at the point 106 between the first and second containment ends 102 and 104. The hinge 150 can comprise any number of rotatable elements such as a barrel hinge, living hinge or other rotatable mechanism. Further, where the hinge itself is not sufficiently biased to hold the shell housing closed, one or more securing tabs 101 and 103 can be provided on at least one of the first and second containment ends 102 and 104 to secure the closure between the first end 102 of the housing 100 and the second end 104 of the housing 100. In an exemplary embodiment shown, the securing tabs 101 and 103 can comprise a deflectable member having an inclined detent at an end thereof, which can be deflected by contact with corresponding openings 105 and 107 provided in at least one of the first and second ends 102 and 104 opposite the hinge 150 of the housing 100, and releasably secured therein. In yet other embodiments of the present invention, other elements such as a biased hinge or press fit can be used to secure the closure between the first end 102 of the housing 100 and the second end 104 of the housing 100.

As also illustrated in FIG. 4, the facing surfaces of the first and second containment ends 102 and 104 of the housing 100 comprise interior access to the openings 108-118 for receiving and storing used pen needles. Specifically, a series of openings 152-162 provide interior access to the openings 108-118 of the first and second opposite containment ends for receiving and storing used pen needles after removal of one or more of the new pen needles that are accessible after removal of the covers 120-130 at the opposite ends of the first and second containment ends 102 and 104. In an exemplary embodiment of the present invention, the openings 108-118 and 152-162 are substantially round and contain therein slidable internal holders 164-174 which separate the openings 108-118 and 152-162 and provide a mechanism to secure the new pen needles at one side, and secure used pen needles when inserted at an opposite side.

Figure 5:
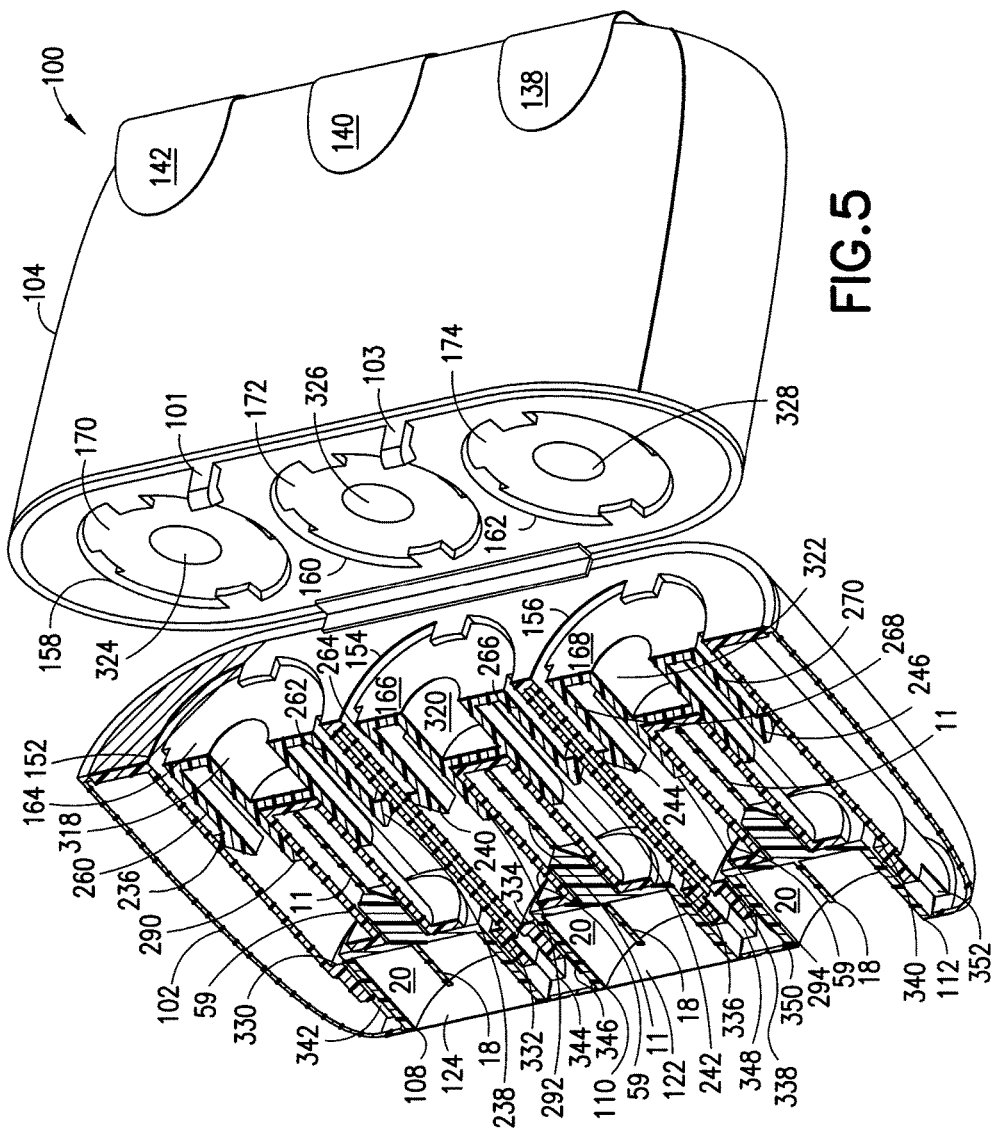
FIG. 5 is a sectional view of the device of FIG. 3 illustrating individual needle assemblies in at least one of the first and second opposite containment ends according to an exemplary embodiment of the present invention.

As shown in greater detail in FIG. 5, slidable internal holders 164-174 can be provided and are configured to releasably secure the shield 59 of the new pen needle, and to then be pulled forward when the new pen needle is removed and lock at a forward position, and thereby create an interior space, accessible from the facing surfaces of the first and second ends 102 and 104 of the housing 100, for a used pen needle to be inserted and stored. To do so, the slidable internal holders 164-174 can also be provided and configured to secure the used pen needle when inserted into the interior space, accessible from the facing surfaces of the first and second containment ends 102 and 104 of the housing 100.

Figure 6:
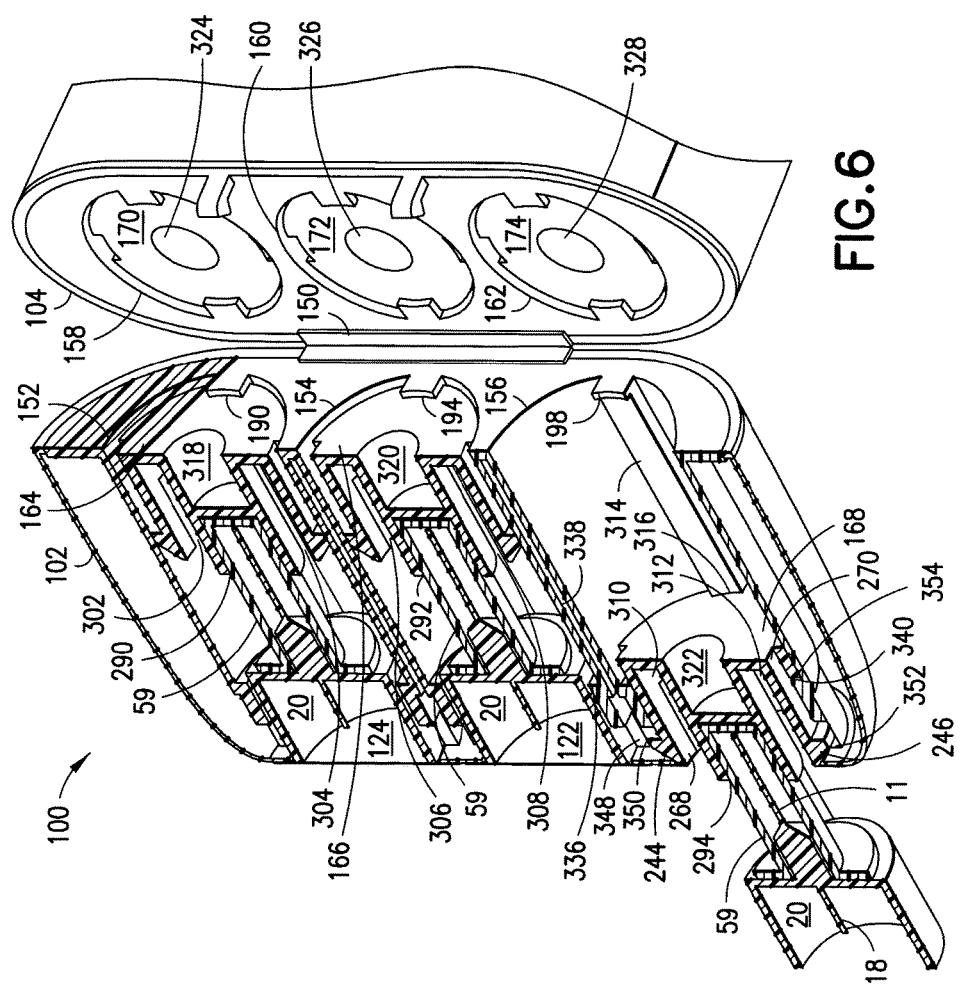
FIG. 6 is an enlarged sectional view of the device of FIG. 3 illustrating a track of motion of the removal of one new pen needle assembly from the multi-pack assembly according to an exemplary embodiment of the present invention.

The slidable internal holders 164-174 have sides facing the openings 108-118 and which releasably secure the capped patient end side of the new pen needles, and side facing interior openings 152-162 to secure the used pen needle when inserted, and provide separation members between each of the spaces. As shown in FIGS. 4 and 5, each of slidable internal holders 164-174 have a flat second side which is configured to substantially fill the openings 152-162 and are trapped within each of openings 152-162 by a series of tabs 188-210 which extend a distance from an inner circumference of the openings 152-162 to prevent escape of the slidable internal holders 164-174. Further, as shown in FIG. 6, each of tabs 188-210 are extended from ribs 314

(repeated in each opening, but only one shown for illustrative purposes) which are disposed along an inner wall of each of the openings 152-162 and which guide a notch 316 (repeated on each slidable internal holder, but only one shown for illustrative purposes) in each of the slidable internal holders 164-174.

Further, each of the second ends of the slidable internal holders 164-174 comprise substantially circular apertures 318-328 as shown in FIG. 5 to provide an entrapment opening for the used pen needles, and which are disposed directly opposite from substantially circular apertures 290-294 (repeated on each slidable internal holder, but only three shown for illustrative purposes) to provide an entrapment opening for the new pen needle inner shield 59 at the first side of each slidable internal holders 164-174 as described in greater detail below.

As also shown in FIGS. 4 and 5, each of the second sides of the slidable internal holders 164-174 have one or more notches 212-234 to provide a degree of clearance for inclined projections 236-246 (repeated on each slidable internal holder, but only six shown for illustrative purposes) disposed at ends of flexible members 260-270 (repeated on each slidable internal holder, but only six shown for illustrative purposes) and which are elastically biased toward contact with an inner wall of each of openings 152-162. Such contact serves a number of purposes, including but not limited to, slightly opposing movement of the slidable internal holders 164-174. Further, as the slidable internal holders 164-174 are moved from a position as shown in FIG. 5, to a position shown in FIG. 6 (in regard to the single example shown), as pulled by the removal of the new pen needle once attached to a pen device (not shown), the inclined projections 236-246 contact shoulders 330-340 (present in each opening, but only six shown for illustrative purposes) near an end of each of openings 152-162 and at a point near openings 108-112, and are deflected inward until pulled past the shoulders 330-340 (present in each opening, but only six shown for illustrative purposes) disposed upon an inner wall of the respective openings. At this point, the inclined projections 236-246 return to a non-deflected state into openings 342-352 (present in each opening, but only six shown for illustrative purposes) and now secure the slidable internal holders 164-174 at the opposite end of the openings 152-162 and at a point near openings 108-112. Once in such a position, for example, the shield 59 attached to the pen needle, is pulled free with the pen needle from the circular aperture 290 of the first end of the slidable internal holder 164 as shown in FIG. 6 (in regard to the single example shown), or the pen needle is pulled free from the shield 59 which is left in the housing shell.

The first end of each of the slidable internal holders 164-174 comprise central apertures 290-294 (present on each slidable internal holder, but only three shown for illustrative purposes) configured to releasably secure the new pen needle inner shield 59 within each of the openings 108-118. To do so, an exemplary embodiment of the present invention can provide such central apertures 290-294 (present on each slidable internal holder, but only three shown for illustrative purposes) as a substantially circular opening of a diameter and depth sufficient to tightly hold the new pen needle shield 59 when in position, but release the new pen needle shield 59, still attached to the new pen needle, when the pen needle is removed. That is, removal of the needle is achieved either through the release of the needle and shield 59 together from the housing shell, requiring the user to remove the inner shield before use, or through the release of the needle from the shield 59 leaving the shield 59 in the housing shell. Relief openings 302-312 (present on each slidable internal holder, but only six shown for illustrative purposes) can be provided surrounding each central apertures 290-294 and provide a space for deflection of the members 260-282 and inclined projections of 236-258.

As noted above, each of the passages between openings 152-162 and openings 108-118 include an inner wall upon which members 314 are used to guide the slidable internal holders 164-174 through contact with the notches 316 in each of the slidable internal holders 164-174. In an exemplary embodiment of the present invention, the members 314 are formed as a rail disposed on the inner wall of the passages between openings 152-162 and openings 108-118. In doing so, the members 314 are used to guide the slidable internal holders 164-174 through contact with the notches 316 in each and are also provided as protrusions for preventing rotation of the new pen needle and the used pen needle contained therein, or inserted therein, to allow the pen needle to be attached and detached from the pen and from the housing shell. Specifically, where the central apertures 290-294 releasably secure the new pen needle shield 59 within each of the openings, the members 314 and notches 316 prevent rotation of the new pen needle to allow the new pen needle to be attached and detached from the pen device and from the housing shell. In a similar manner, where the apertures 318-328 secure the used pen needles within each of the openings, the members 314 and notches 316 prevent rotation of the used pen needle to allow the used pen needle to be detached from the pen while held in the housing shell.

Further, at a point near the end of slidable travel of the slidable internal holders 164-174, the inner wall of the openings comprises the shoulders 330-340 to contact similar shoulders 354 (present on each slidable internal holder, but only one shown for illustrative purposes) of the slidable internal holders 164-174 and stop slidable travel in a first (forward) direction. However, the inclined projections 244 and 246 are deflected and pass over the shoulders 338 and 340, return to a non-deflected state into openings 350 and 352, and are then captured in the openings 350 and 352 provided in the inner wall and secure the slidable internal holders 164-174 at the opposite end of the openings and prevent slidable travel in a second (rearward) direction. In this position, the slidable internal holders 164-174 are prevented from either further forward or rearward travel, and cannot be rotated.

Figure 7:
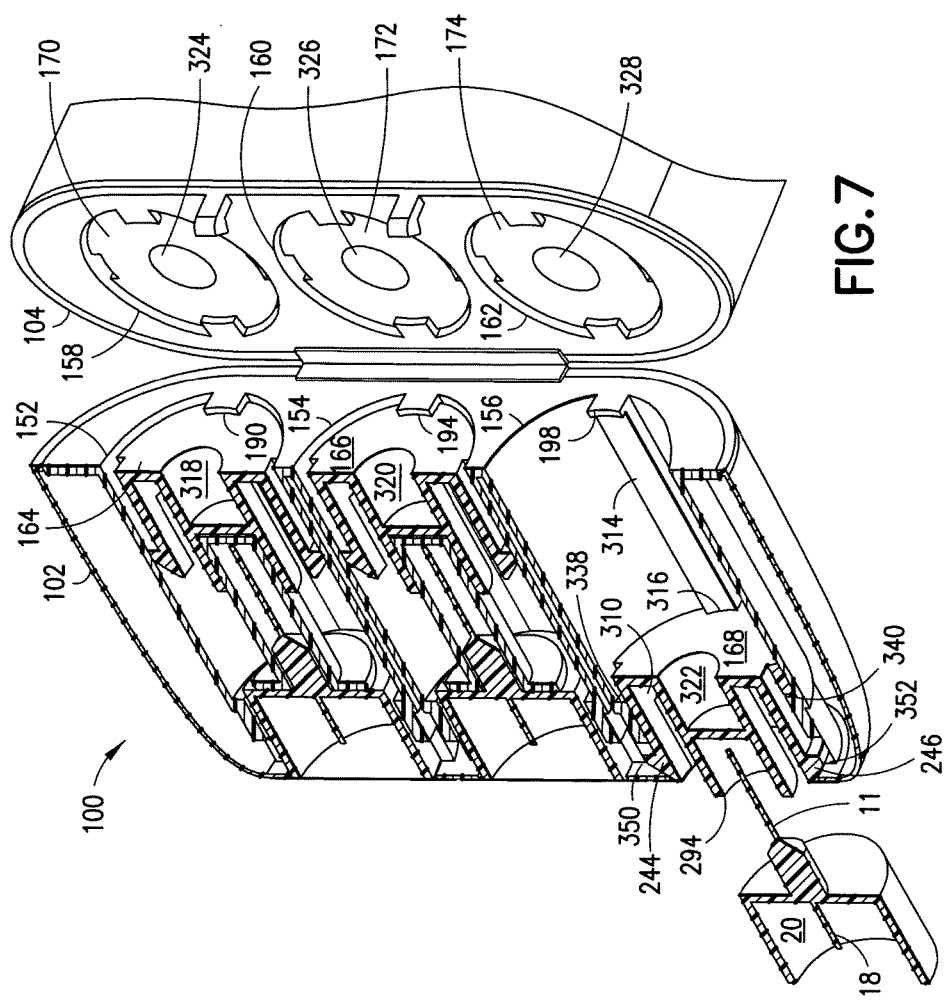
FIG. 7 is an enlarged sectional view of the device of FIG. 3 with one new pen needle removed according to an exemplary embodiment of the present invention.

As shown in FIGS. 6 and 7, once travel of the slidable internal holders 164-174 is stopped in this manner, the new pen needle is pulled free of the housing 100 and the shield 59 can then be removed for device usage, or the needle can be released from the shield 59 which is left in the housing shell. Further, once travel of the slidable internal holders 164-174 is stopped in this manner, the used pen needle can be placed within the now open space provided by the movement of the slidable internal holders 164-174 during new pen needle removal, engaging the apertures 318-328 to secure the used pen needle within the openings and the housing closed for storage.

Figure 8:
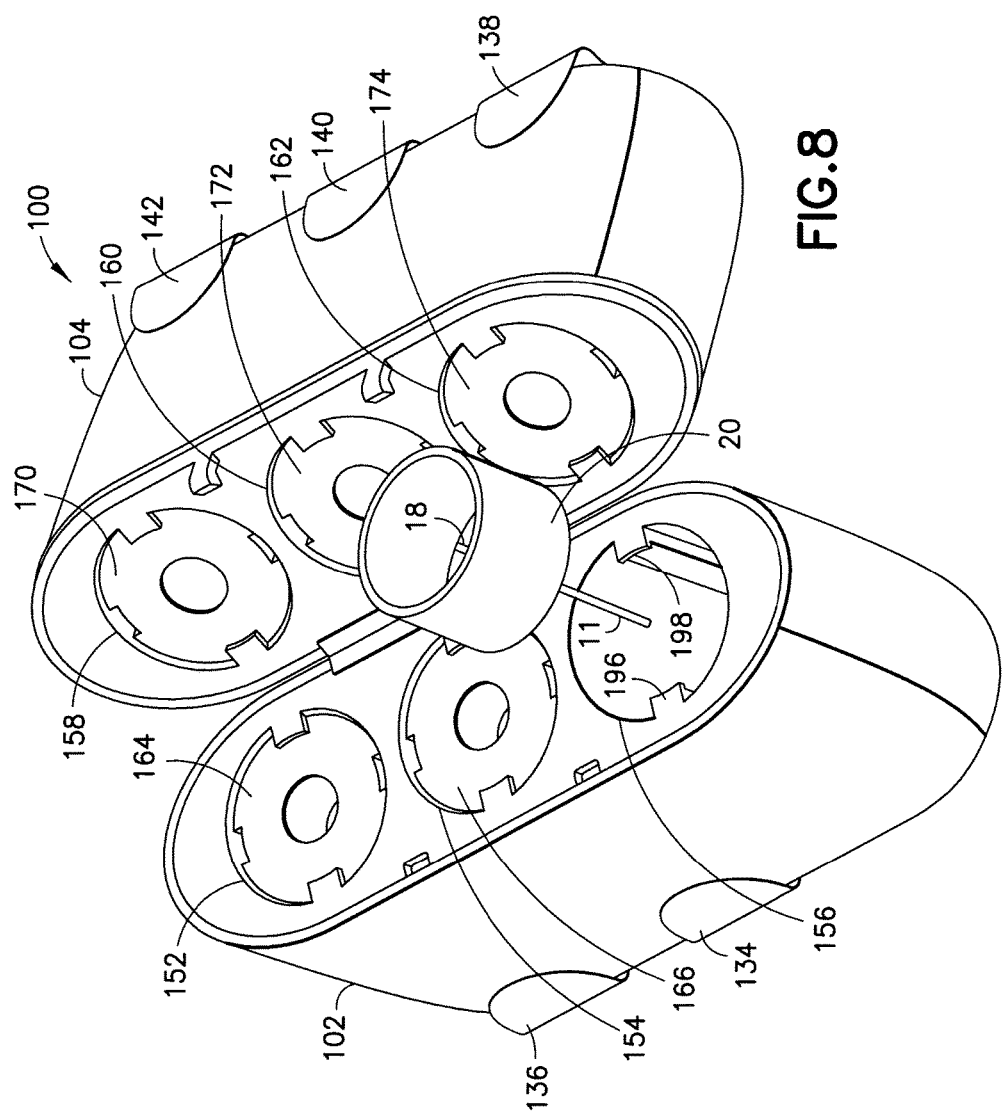
FIG. 8 is an enlarged sectional view of the device of FIG. 4 illustrating used pen needle return and storage in the multi-pack assembly according to an exemplary embodiment of the present invention.

The new pen needle removal operations can be performed with the housing 100 open or closed, as the new pen needle is accessible via the covered openings 108-118 at the ends of the housing opposite the hinged point. FIG. 8 illustrates the placement of the used pen needle back into the housing 100 for storage. As shown in FIG. 8, the housing 100 is first opened so a user can access an interior space provided in one of the openings 152-162, created by the removal of the new pen needle as described above, such that the slidable internal holder is now deeply positioned within the opening. Accordingly, the user can insert the used pen needle into the opening 156 and engage the second end of the slidable internal holder (not shown). Specifically, the used pen needle is engaged with the second end of the slidable internal holder thereby securing the used pen needle in the opening 156, and the pen is unscrewed or otherwise detached from the used pen needle now securely held deeply within the opening 156. The housing 100 can then be closed and the used pen needle safely stored, while new pen needles are also safely stored and accessible in the same housing.

Figure 2A:
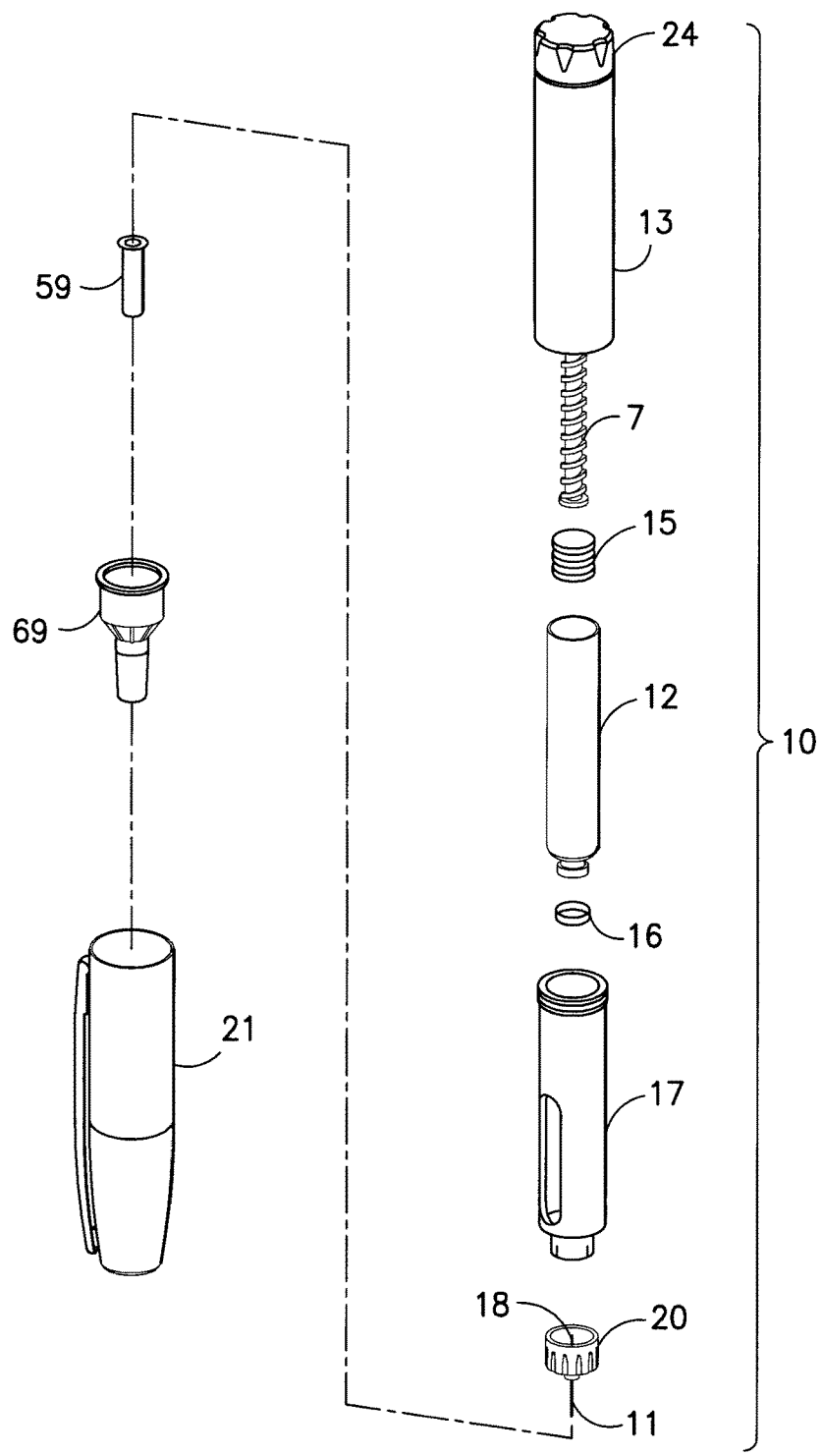
FIG. 2A is an exploded perspective view of the components of the drug delivery pen of FIG. 1.
Figure 2B:
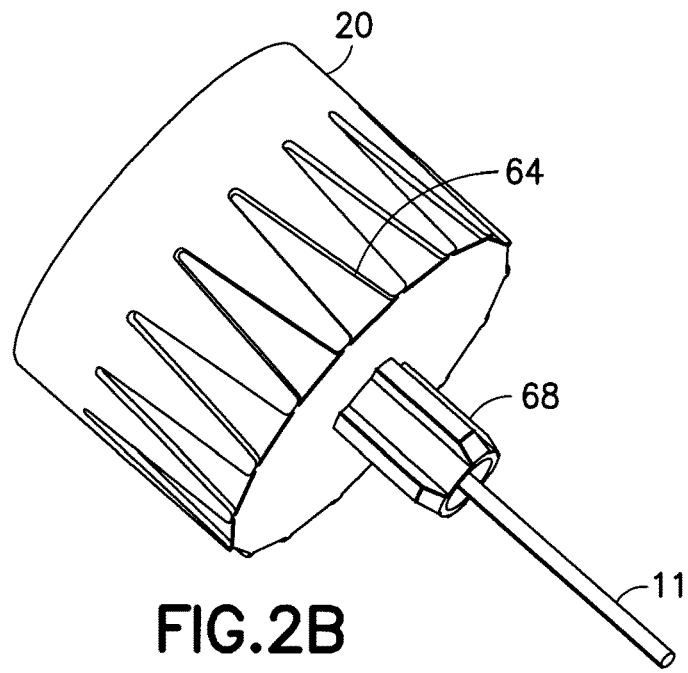
FIGS. 2B and 2C are perspective views of the pen needle for use with the drug delivery pen of FIG. 1.
Figure 2C:
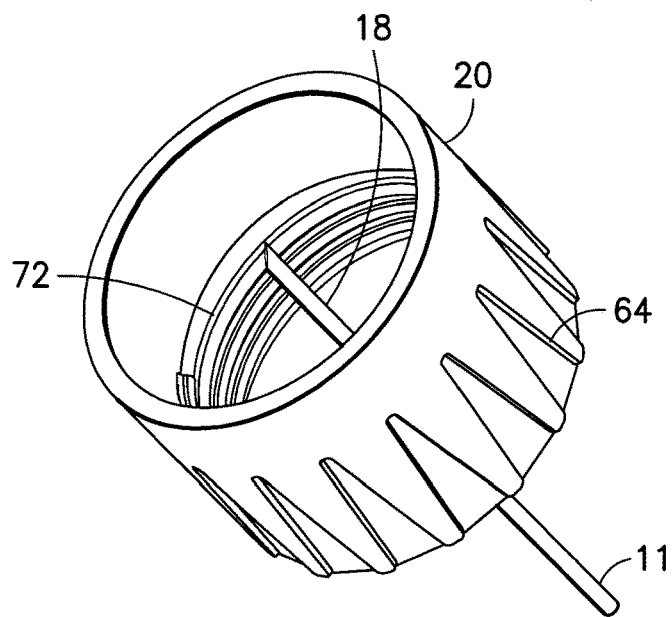

As noted above, FIGS. 2B and 2C are perspective views of the pen needle of FIG. 2A wherein the pen needle includes the hub 20, protrusion 68 and patient needle 11. The septum-penetrating needle cannula 18 disposed within the non-patient end of the hub 20 fluidly communicates with the patient needle 11, and the interior of the non-patient end of the hub 20 includes threads or other features 72 for connection with the pen injector. In these or other exemplary embodiments of the present invention the pen needle can omit one or more of the above features as long as sterility of both the patient and non-patient ends of the cannula is maintained. For example, an exemplary pen needle can also be provided having a hub and cannula assembly only.

In another exemplary embodiment of the present invention, the multi-pack assembly 100 can be constructed of one or more of a polycarbonate, polyethylene, polypropylene and acrylonitrile butadiene styrene material, but is not limited thereto. Further, the multi-pack assembly 100 and/or the covers 120-130 can be color-coded or otherwise marked to simplify identification of the new pen needles stored therein. Still further, the exemplary embodiment shown comprises first and second containment ends, 102 and 104, respectively, that are rotatably joined at a point 106, but in other embodiments of the present invention the first and second containment ends can be non-rotatably joined, or only one containment end can be provided and a hinged cap provided in place of the omitted containment end.

Figure 9:
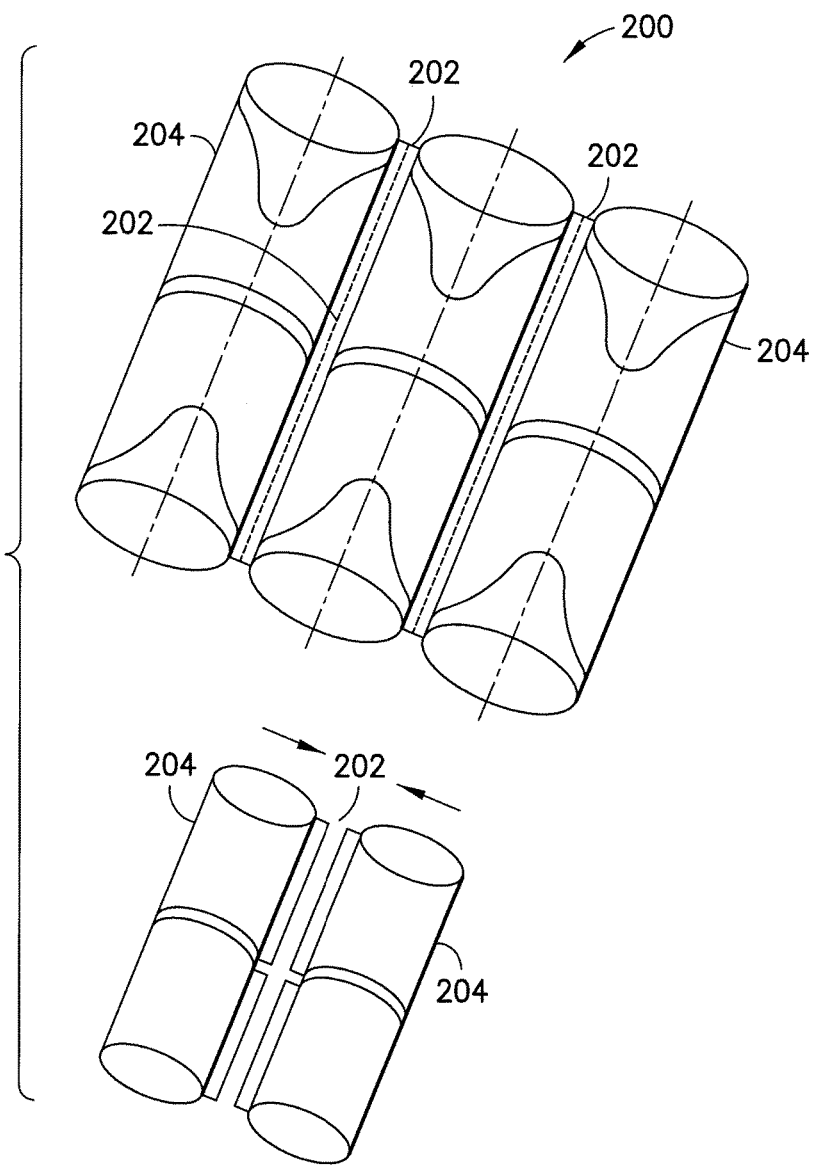
FIG. 9 is a perspective view of a multi-pack assembly having user-separable packs according to another exemplary embodiment of the present invention.

In yet other embodiments of the present invention, the multi-pack assembly can be divided by the user into sets of two, four, or similar sets thereby allowing the user to select the number of new pen needles that are to be carried. FIG. 9 is a perspective view of a multi-pack assembly having such user-separable containment ends according to another exemplary embodiment of the present invention. In the exemplary embodiment show, the multi-pack assembly 200 is perforated between containment ends to allow a user to tear off, or break away, two containment ends along the hub central axis, while still maintaining sterility as well as the ability to store new and used pen needles as described above. In such an embodiment, a perforated thin section 202 is provided between each containment end 204 to allow such user separation.

In yet other embodiments of the present invention, the multi-pack assembly can be enlarged by the user by adding additional sets of two, four, or similar sets of containment ends, thereby allowing the user to select the number of new pen needles that are to be carried. For example, the multi-pack assembly can have connectors between containment ends to allow a user to disconnect or connect additional containment ends, while still maintaining sterility as well as the ability to store new and used pen needles as described above. In such an embodiment, a male detent can be provided on one side of each containment end, and a female opening can be provided on an opposite side of each containment end, such as a rectangular member and opposite opening, to allow such user separations and combinations in a snap-fit manner. Alternatively, a sliding connector mechanism could be used to attach and detach containment ends of needles, such as through the provision of a fail and guide, or dovetail mechanism.

Further, in these or other exemplary embodiments of the present invention, a lock-out system and method can be provided such that after the use of the final needle, the user can manually lock the housing (i.e., manually lock the housing closed) to allow for safe disposal. For example, a manual lock can be provided on the needle storage assembly, thereby allowing the user to manually lock the storage assembly after final use to allow for safe disposal thereof and prevent reuse. In these and other exemplary embodiments of the present invention, an emergency needle feature can also be provided wherein at least one new or used needle can remain accessible, such that the user has access to at least one of the new or used needles for use in case of an emergency. Alternatively, in yet other embodiments of the present invention, only one needle can be provided as always accessible, thereby providing an available needle for use in case of emergency. The other pen needles can be locked into the storage assembly and can no longer be accessible.

In yet another exemplary embodiment of the present invention, an alternate design can be provided to simplify the inner mechanics of the device and for sterility barrier issues. For example, the device can comprise only one open end for each pen needle. The opening can be on the inside and accessed only when the hinge of the device is opened up, or the opening can be on the outside where no living hinge would be required. Further, a cover can be provided on either of these openings, and the new pen needle would be removed, and the used pen needle returned to the same space. In such an exemplary embodiment, much of the inner elements and mechanics of the device described above could be eliminated, thereby simplifying the manufacturing processes.

In the exemplary embodiment of the present invention, a sterility barrier is provided on the patient end of the pen needle, such as provided by the tortuous path of the shield, but such tortuous path of the patient end of the pen needle can be improved. For example, a solid piece can be provided at the end of the patient end of each pen needle wherein such an exemplary solid piece can be configured to fit flush against the wall of the cavity or openings in the housing shell, and the solid piece can be sealed or otherwise secured to the inner wall of the housing shell in some manner, such as through a heat sealing operation or adhesive, to secure the solid piece to the wall. Thereafter, applying a limited pulling force can then be used to break the seal of the solid piece from the wall and allow the new pen needle to be pulled out of the cavity of the housing shell. Such an exemplary seal can be configured to provide or supplement the sterility barrier on the patient end.

In yet another exemplary embodiment of the present invention, the device can include the placement of a cover on each end of the individual cavities to provide a sterility barrier on each end of the pen needle. In this exemplary embodiment, the cover on the non-patient contacting end would have to be removed prior to attachment of the pen needle to the pen. Then, the cover on the patient side of the cavity would have to be removed prior to returning the used pen needle to the device.

As noted above, in accordance with another aspect of the present invention, a multi-pack assembly for containing and then dispensing one or more new pen needles, and receiving and then safely and securely storing used pen needles, can be provided by a device including a plurality of pen needles individually contained in a tube-shaped structure. A sterility barrier for each new pen needle should be provided and is formed by covers that cover a non-patient end of each pen needle, and each pen needle can be contained in a separate, individually accessible section or unit of the tube structure, and adjacent units of the tube structure can be hingedly connected.

Figure 10:
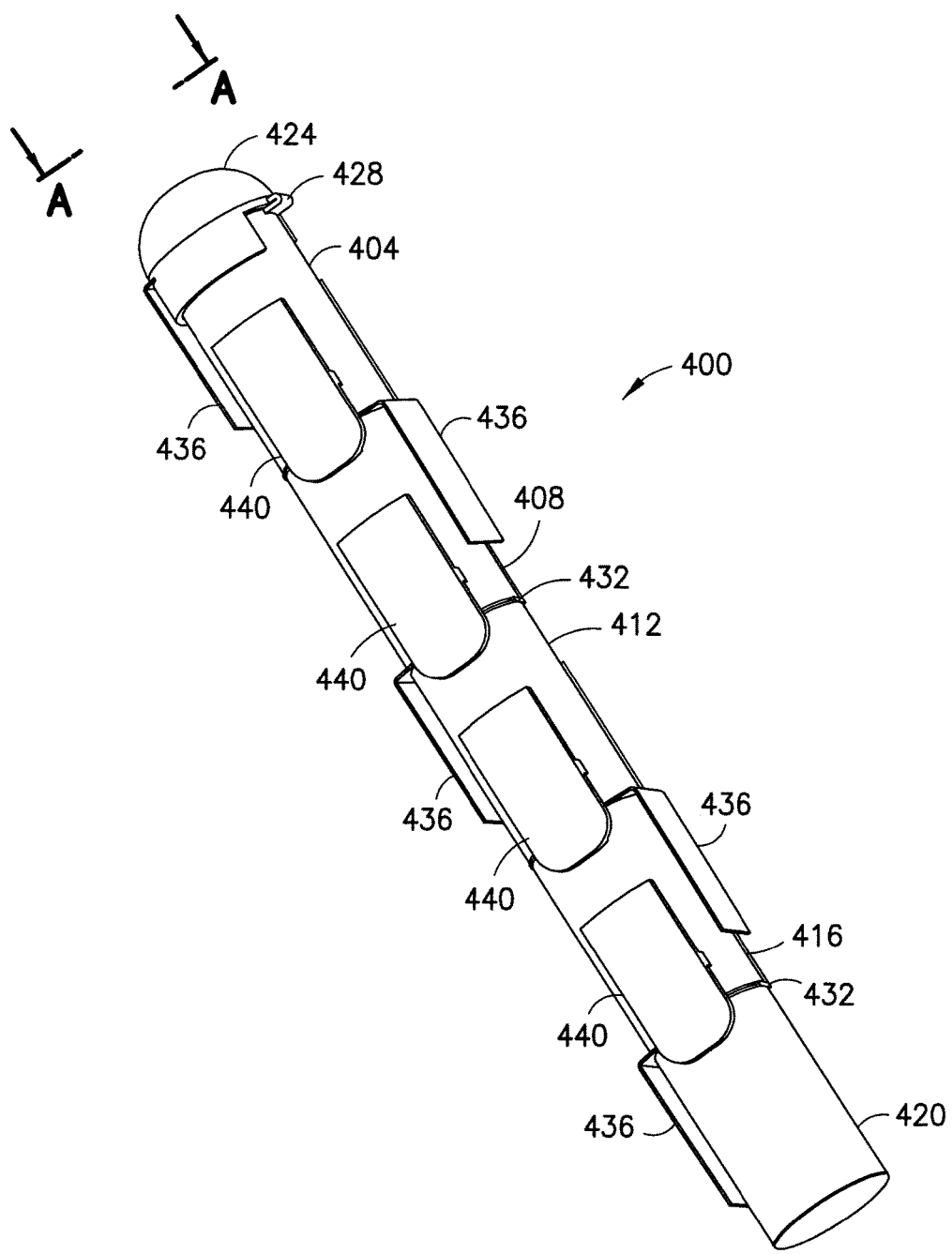
FIG. 10 is a perspective view of a flip-open multi-pack assembly according to another exemplary embodiment of the present invention.
Figure 11:
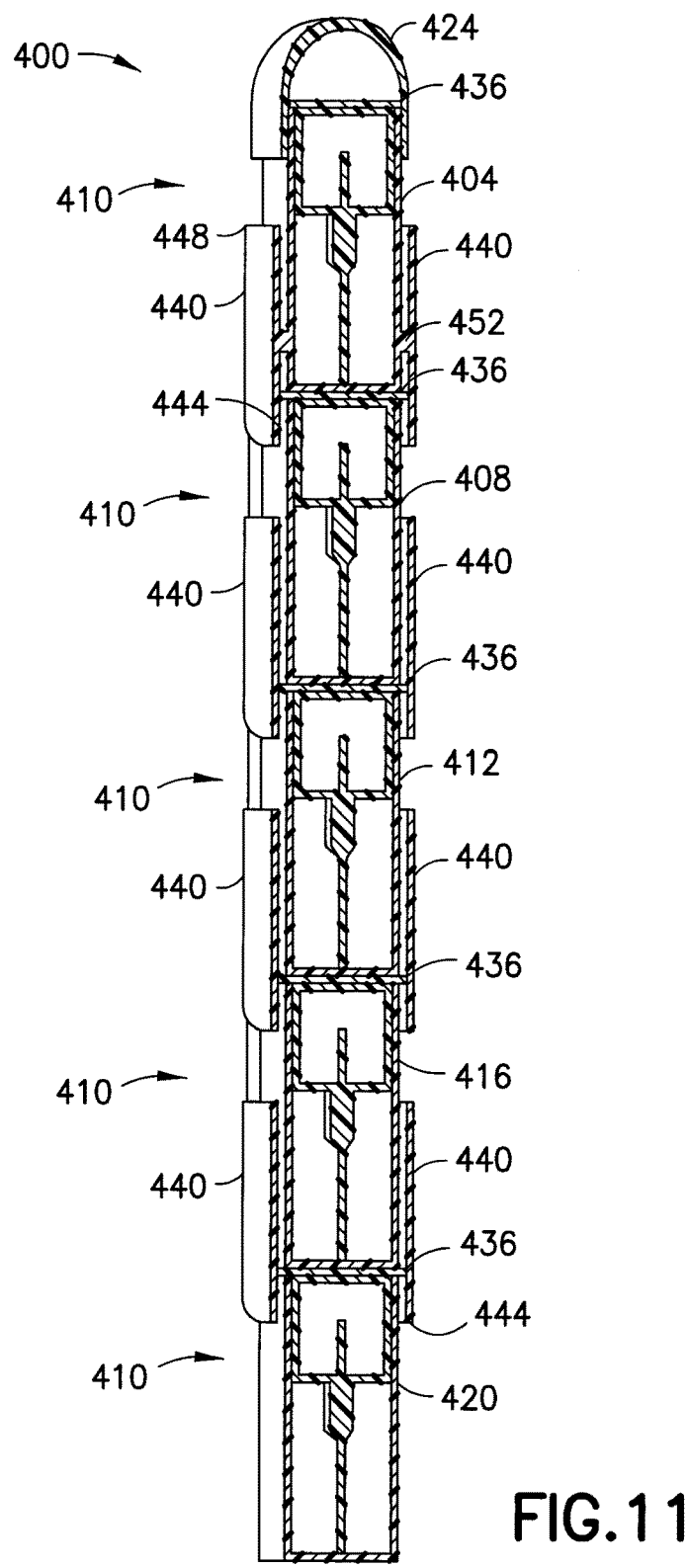
FIG. 11 is an enlarged sectional view of the device of FIG. 10 according to an exemplary embodiment of the present invention.

FIG. 10 is a perspective view of a flip-open multi-pack assembly according to another exemplary embodiment of the present invention, and FIG. 11 is an enlarged sectional view of the device of FIG. 10. FIG. 10 is a perspective view of a flip-open multi-pack tube assembly 400 in accordance with an embodiment of the present invention. The assembly 400 includes a plurality of pods or storage units for storing a plurality of pen needles 410. For example, as shown in FIG. 10, the assembly 400 includes first through fifth storage units 404, 408, 412, 416 and 420. The plurality of pen needles are individually contained within the respective storage units 404-420. The hingedly connected individual storage units 404-420 replace the inner shield and the outer cover of FIG. 2A, in addition to other functions as will be described. However, in other exemplary embodiments the inner shields can be employed in combination with pen needles and storage units 404-420.

As shown in FIG. 10, the first storage unit 404, unlike the remaining storage units, has a lid 424 which is connected to the first storage unit 404 by a lid hinge 428. Additionally, a hinge 432 connects each of the remaining storage units 408-420 to its adjacent storage unit. As partially shown in FIG. 10, according to one embodiment, the lid hinge 428 and the hinges 432 are alternately disposed on opposing sides of the assembly 400 so that, as described in greater detail below, each storage unit is opened in an opposing direction than its adjacent storage unit(s). However, in yet other exemplary embodiments of the present invention, the lid hinge 428 and the hinges 432 may be all disposed on one side without departing from the scope of the present invention. The lid hinge 428 and the hinges 432 may be, for example, living hinges. A living hinge is not described in greater detail herein, as it would be understood by those knowledgeable of the art.

According to one embodiment, sterility covers 436 provide a sterility barrier for each of the storage units 404-420. As will be described in greater detail below, when each of the storage units 404-420 is accessed, the sterility cover 436 is removed to access the sterile pen needle contained therein. The sterility covers should be provided to cover the openings and the new pen needles contained therein. The sterility barriers can be constructed of paper, metal foil, plastic or similar materials, and attached to cover the openings via adhesive, heat seal, ultrasonic welding or other suitable means, and each of the covers can be provided with a tab element to allow a user to easily grasp and remove the tabs and covers. In an exemplary embodiment of the present invention, the tabs of the sterility covers 436 can be provided with a different degree of adhesion, to allow a user to easily grasp and lift the tabs. The sterility covers 436 can be further provided with colors, marks or other indicators of the pen needle contained therein.

FIG. 11 is a perspective view in cross-section taken along line A-A in FIG. 10 of the assembly 400. As shown in FIG. 11, each of the storage units 404-420 encapsulates a pen needle 410 with the non-patient end of the pen needle 410 being oriented toward the top of the storage unit. Additionally, as shown in FIGS. 10 and 11, a plurality of closure members or tabs 440 are disposed on the storage units, each closure member 440 selectively engaging an adjacent storage unit (408-420) to close the interior of the adjacent storage unit (408-420). Conversely, as will be described in greater detail below, each closure member 440 selectively disengages from the adjacent storage unit (408-420) to provide access to the interior of the adjacent storage (408-420) unit by rotation about the connecting hinges 432.

According to one embodiment as shown in FIG. 11, closure members 440 are disposed in pairs on opposing sides of the first through fourth storage units 404-416. Additionally, as will be described in greater detail below, each of the closure members 440 has an engaging member 444 disposed at a first end thereof for selectively engaging and disengaging from the adjacent storage unit (408-420). Further, as will be described in greater detail below, each closure member 440 has a user portion 448 disposed at a second end thereof for interaction with a user. Moreover, as shown in FIG. 11, each of the closure members 440 is connected to its corresponding storage unit (404-416) via a web 452. The web 452 provides structural connection between the closure members 440 and the corresponding storage units, and is also sufficiently flexible to act as a pivot and allow rotation of the closure members 440 relative to the corresponding storage units.

Figure 12:
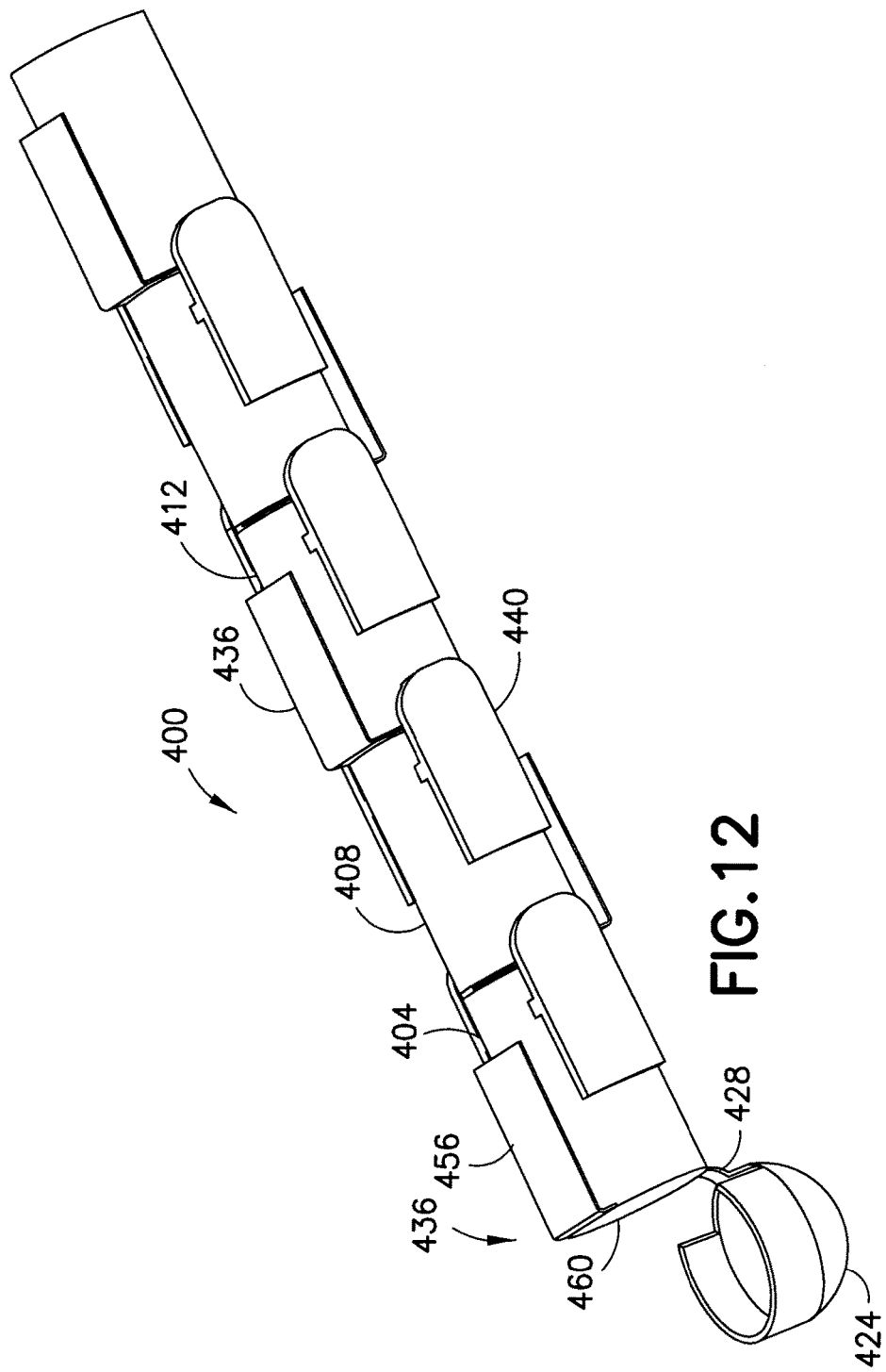
FIG. 12 is a perspective view of the device of FIG. 10 preparing one new pen needle for removal according to an exemplary embodiment of the present invention.
Figure 13:
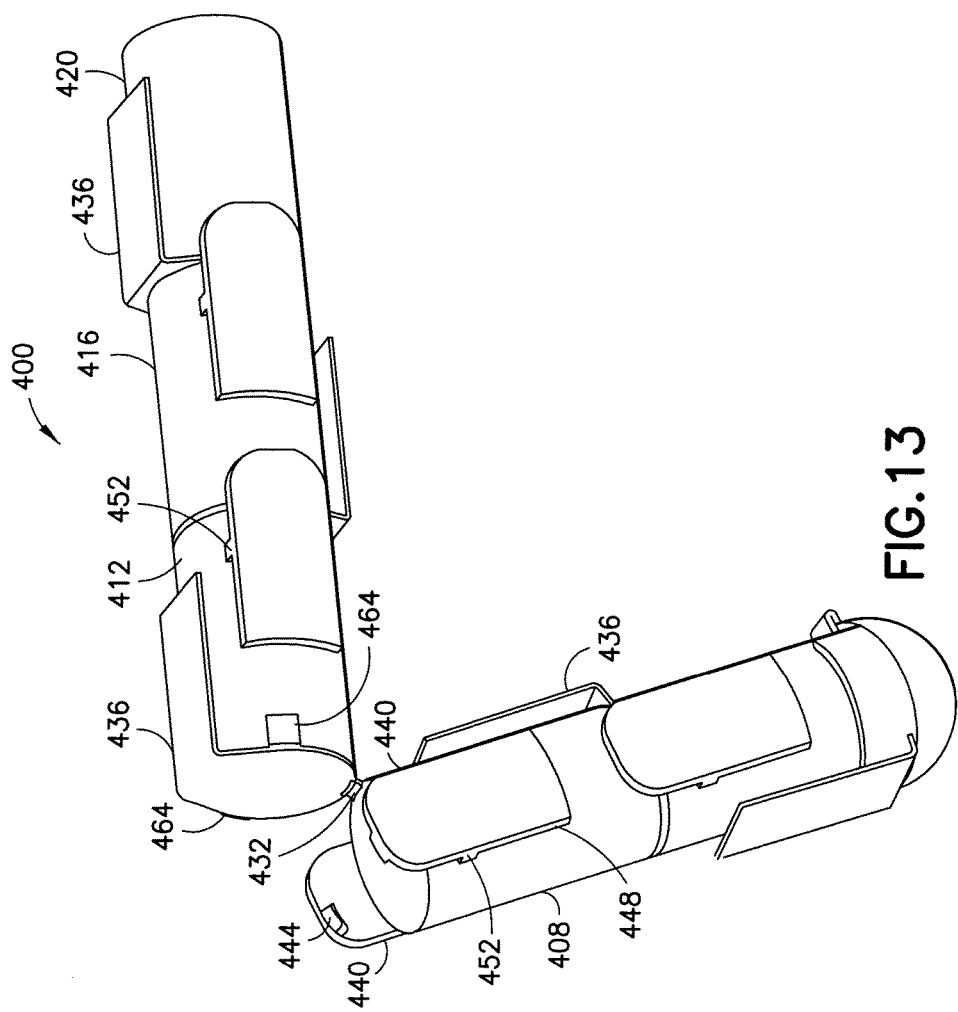
FIG. 13 is a perspective view of the device of FIG. 10 preparing another new pen needle for removal according to an exemplary embodiment of the present invention.
Figure 14:
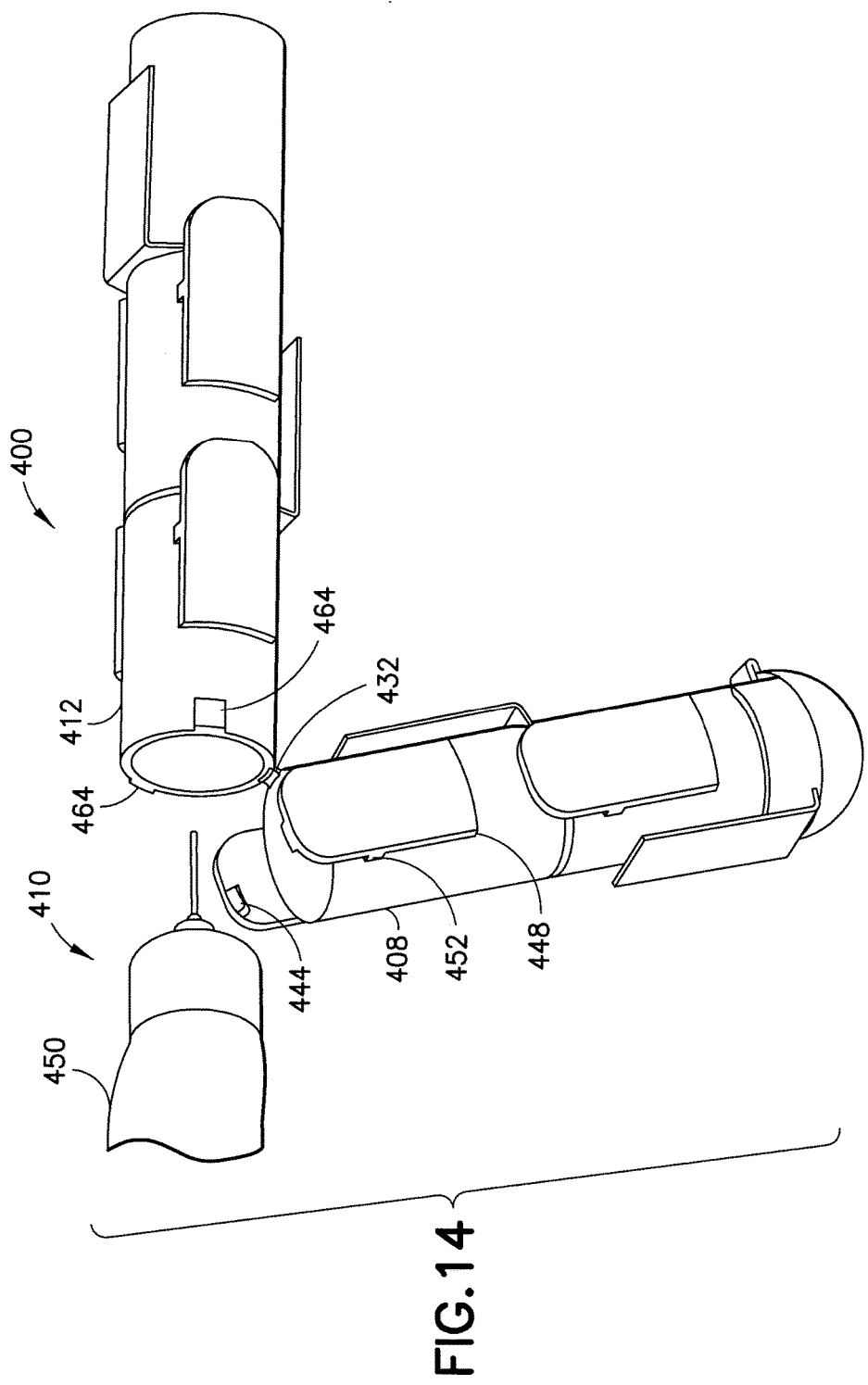
FIG. 14 is a perspective view of the device of FIG. 10 with one new pen needle removed according to an exemplary embodiment of the present invention.

With reference to FIGS. 12-14, the operation of the assembly 400 will now be described. FIGS. 12 and 13 are perspective views of the device of FIG. 10 preparing a new pen needle for removal, and FIG. 14 is a perspective view of the device of FIG. 10 with a new pen needle removed according to an exemplary embodiment of the present invention.

As shown in FIG. 12, to access the pen needle 410 in the first storage unit 404, the user rotates lid 424 about lid hinge 428 to reveal the sterility cover 436. As shown in FIG. 12, the sterility cover 436 includes a tab portion 456 and a closure portion 460. Subsequent to opening the lid 424, the user grasps and lifts the tab portion 456 to peel off the cover portion 460, which is adhered to the first storage unit 404. Removal of the sterility cover 436 provides access to the non-patient end of the pen needle 410 contained within the first storage unit 404. The user then connects a pen injector 450 to the non-patient end of the pen needle 410 for use.

After use, the user returns used pen needle 410 to the same storage unit it came from. In the example above, the user removed the pen needle 410 from the first storage unit 404, and thus can return the used pen needle 410 to the first storage unit 404, disengage the pen injector 450 from the pen needle 410, and close first storage unit 404 by rotating the lid 424 about the lid hinge 428.

Subsequent removal of new pen needles, in contrast to accessing the pen needle in the first storage unit 404, by accessing a pen needle 410 in any of the second through fifth storage units 408-420 is accomplished via a different method. For example, as shown in FIG. 13, to access the pen needle 410 in the third storage unit 412, the user grasps and squeezes the user portions of closure members 440 of the second storage unit 408. Because of the flexibility of the web 452, the squeezing rotates the closure member 440 with respect to the second storage unit 408. More specifically, the squeezing rotates the engaging members 444 outwardly with respect to the second storage unit 408, thereby disengaging the engaging members 444 from the third storage unit 412.

As shown in FIG. 13, the third storage unit 412 has a pair of retaining members 464 corresponding to the engaging members 444 of the closure members 440 of the second storage unit 408. According to one embodiment, the retaining members 464 are bosses extending from opposing sides of the third storage unit 412. In yet other exemplary embodiments, the retaining members 464 are detents recessed from opposing sides of the third storage unit 412. When closed, the hook-like engaging members 444 engage the retaining members 464. However, when the closure members 440 are squeezed and rotated by the user, the engaging members 444 release from the retaining members 464. As the closure members 440 are disposed on the first through fourth storage units 404-416, corresponding retaining members 464 are disposed on the second through fifth storage units 408-420.

As shown in FIG. 13, after disengaging the closure members 440 from the retaining members 464, the user rotates the first and second storage units 404 and 408 away from the third through fifth storage units 412-420 via hinge 432. Subsequently, similar to accessing the pen needle 410 in the first storage unit 404, the user removes the sterility cover 436, and connects the pen injector 450 to the non-patient end of the pen needle 410 for use as shown in FIG. 14. After use, the user then returns the pen needle 410 to the third storage unit 412, disconnects the pen injector 450 from the pen needle 410, and closes the assembly 400 by rotating the first and second storage units 404 and 408 about the hinge 432 until the engaging members 444 of the closure members 440 of the second storage unit 408 engage the retaining members 464 of the third storage unit 412.

Figure 15:
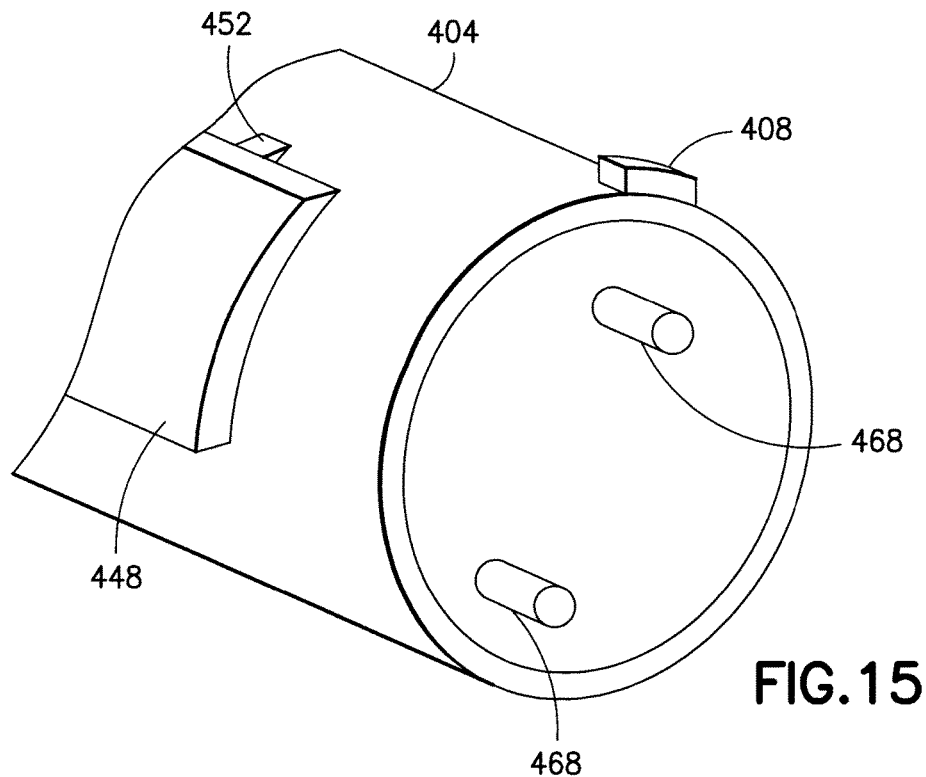
FIG. 15 is an enlarged perspective view of a dispensing end of a first storage unit of the device of FIG. 10 according to an exemplary embodiment of the present invention.
Figure 16:
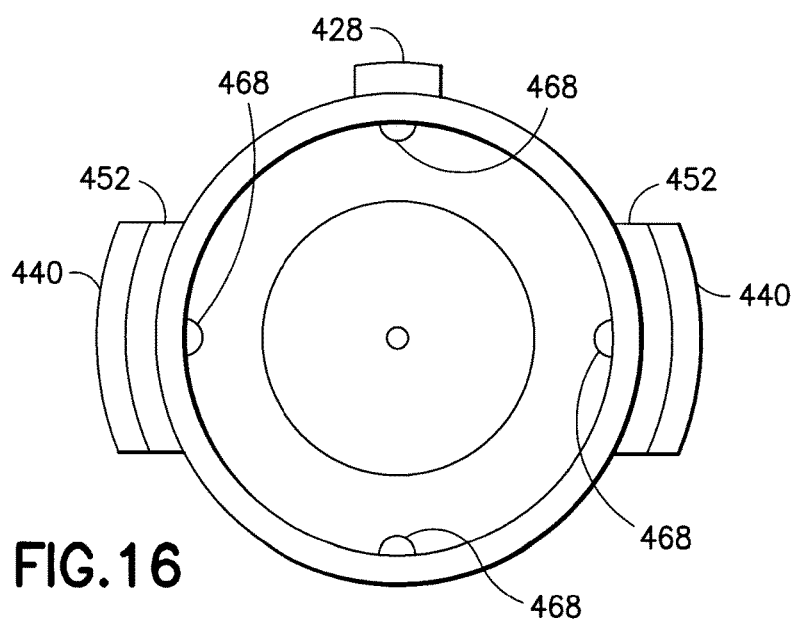
FIG. 16 is an end view of the dispensing end of the first storage unit of FIG. 15 according to an exemplary embodiment of the present invention.

FIG. 15 is an enlarged perspective view of a dispensing end of the first storage unit 404 and FIG. 16 is an end view of the dispensing end of the first storage unit 404. For clarity, the lid 424 and the pen needle 410 are not illustrated in FIGS. 15 and 16. As shown in FIGS. 15 and 16, the dispensing end of the first storage unit 404 includes a plurality of anti-rotation/retaining structures 468. Only the first storage unit 404 is shown, but each of the storage units 404-420 includes such anti-rotation/retaining structures 468. At the dispensing end of the first storage unit 404, the anti-rotation/retaining structures 468 work in conjunction with the hub of a pen needle to prevent rotation of the pen needle when the pen needle is in a dispensing position. For example, when the pen needle is in the dispensing position within the first storage unit 404 and the anti-rotation/retaining structures 468 are engaged with the ribs 64 (see FIGS. 2B and 2C) of hub 20, the anti-rotation/retaining structures 468 prevent the pen needle from rotating and permit the user to connect a pen injector or a medicament cartridge to the hub by threading the pen injector or medicament cartridge into the threads 72 of the hub 20. While preventing rotation of the pen needle during connection to the pen injector, subsequent to the connection, the fit between the anti-rotation/retaining structures 468 and the pen needle permits the user to axially withdraw the combined pen injector and pen needle from the first storage unit 404.

Conversely, when returning the used pen needle to the first storage unit 404, the user axially inserts the pen needle into the first storage unit 404 to engage the ribs 64 of the hub 20 with the anti-rotation/retaining structures 468. Subsequent to the engagement, the user rotates the pen injector to unthread the pen injector from the threads 72 of the hub 20, thereby disengaging the pen injector from the pen needle. The fit between the anti-rotation/retaining structures 468 and the pen needle provides some resistance to removal of the pen needle from the first storage unit 404 and prevents the pen needle from simply falling out of the first storage unit 404 subsequent to removal of the sterility cover 436.

Figure 17:
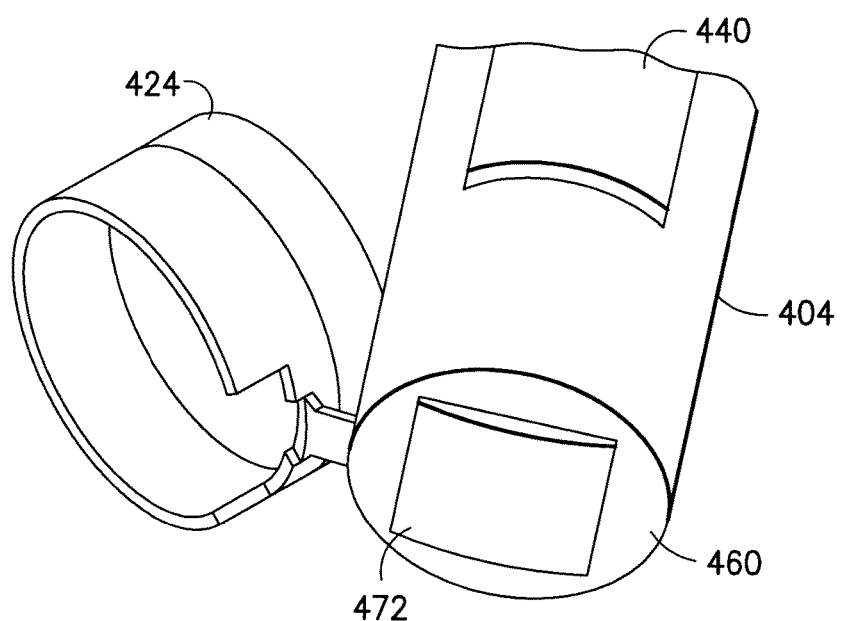
FIG. 17 is a perspective view of a sterility cover according to an exemplary embodiment of the present invention.

FIG. 17 is a perspective view of another embodiment of a sterility cover 136 covering the dispensing end of the first storage unit 404. Whereas, for example, in FIG. 12, the tab portion 456 of the sterility cover 436 is disposed on the outside of the assembly 400, in FIG. 17, the tab portion 472 folds over on top of cover portion 460 and is enclosed by the cover 424 when the cover is closed. Similarly, although not shown, the adjacent storage units 404-416 enclose the tab portions 472 of the remaining sterility covers 436 when closed. In yet other exemplary embodiments of the present invention, the sterility covers 436 can be secured by, and/or removed by the action of opening the cover 424 and/or the adjacent storage units 404-416. In yet other exemplary embodiments of the present invention, a circumferential sterility cover can be provided and can be peeled off prior to access to the individual pen needles. In still other exemplary embodiments of the present invention, the sterility cover 436 can be omitted, and the closure between individual storage units 404-420, as well as the closure between the cover 424 and the first storage unit 404, can be a form-fit or interference-fit tortuous path, thereby providing the sterility barrier. As known to those skilled in the art, a tortuous path closure can be defined as a barrier to airborne microorganisms, accomplished by creating a convoluted pathway to the product, for example, by labyrinth paths or a screw-threaded closure.

Because patients are accustomed to using and transporting pen injectors, one advantage of the exemplary embodiments of the present invention is to provide a compact, convenient apparatus for containing and dispensing new pen needles, and storing used pen needles, in an easy to transport assembly. A lock can be provided on the pen needle storage assemblies, thereby allowing the user to manually lock the storage assembly to allow for safe disposal thereof. Preferably, such locks become functional only after the last pen needle has been used, but embodiments are not limited thereto. In another exemplary embodiment of the present invention, one or more used pen needle remains accessible such that the user has access to a used pen needle in case of an emergency. The other pen needles can also be accessible or locked into the storage assembly.

The foregoing embodiments and advantages are merely exemplary and are not to be construed as limiting the scope of the present invention. Various modifications, alternatives and variations will be apparent to those of ordinary skill in the art, and are intended to fall within the scope of the invention as defined in the appended claims and their equivalents.

What is claimed is:

1. A method for storing both new and used pen needles of an injection apparatus in a single storage assembly, comprising the steps of:
   removing a cover to access a new pen needle secured within an opening of said assembly;
   attaching said new pen needle to a drug delivery pen, wherein said new pen needle is releasably secured within said opening and prevented from rotating; and
   pulling the new pen needle from one end of said opening to remove the new pen needle, wherein such removal motion serves to pull a slidable internal holder within the assembly forward, thereby creating a space at an opposite end of said opening for a used pen needle to be inserted and stored.

2. The method as recited in claim 1, further comprising the steps of:
   opening said assembly at a hinged point between opposite first and second containment ends to allow interior access to said opposite end of said opening for receiving and storing the used pen needle;
   inserting said used pen needle into said opposite end of said opening, engaging an anti-rotation feature, unscrewing a pen injection device from said used pen needle, and leaving said used pen needle in said opening of said assembly; and closing said assembly for storage.

3. The method as recited in claim 2, wherein: said opening comprises one or more openings in each of said first and second containment ends, the one or more openings are adjacent to each other.

4. The method as recited in claim 3, wherein each of said openings of said first and second opposite containment ends comprises a sterility barrier.

5. The method as recited in claim 3, wherein each of said openings of said first and second opposite containment ends can accommodate an inner shield for a patient end of a pen needle, configured to releasably secure said pen needle in each opening.

6. The method as recited in claim 3, wherein each of said openings of said first and second opposite containment ends passes through an entire length of each containment end, respectively.

7. The method as recited in claim 3, wherein one or more of said openings within each of said first and second opposite containment ends of said assembly includes said anti-rotation feature comprising one or more protrusions for holding a pen needle in said opening and preventing rotation of said pen needle.

8. The method as recited in claim 1, wherein said slidable internal holder is configured to be moved through said opening when a new pen needle is removed and lock at a forward position, and to create the space in said opening, opposite said new pen needle removal side and accessible from an interior surface of said assembly, for a used pen needle to be inserted and stored.

9. The method as recited in claim 1, wherein said assembly is constructed of one or more of a polycarbonate, polyethylene, polypropylene and acrylonitrile butadiene styrene material.

* * * * *